United States Patent [19]

Mims et al.

[11] Patent Number: 4,542,993

[45] Date of Patent: Sep. 24, 1985

[54] METHOD OF MEASURING QUALITY OF STEAM IN A FLOW FINE

[75] Inventors: Donald S. Mims, Houston, Tex.; Terry L. Frazier, Paso Robles, Calif.

[73] Assignee: Texaco Inc., White Plains, N.Y.

[21] Appl. No.: 530,844

[22] Filed: Sep. 9, 1983

[51] Int. Cl.⁴ .................. G01K 17/06; G01N 25/60
[52] U.S. Cl. ......................................... 374/42; 374/40
[58] Field of Search ............... 374/42, 24, 54; 73/154

[56] References Cited

U.S. PATENT DOCUMENTS

| | | | |
|---|---|---|---|
| 1,214,853 | 2/1917 | Weil | 374/42 |
| 2,387,717 | 10/1945 | Clarkson | 374/42 X |
| 3,100,395 | 8/1963 | Morley | 374/42 |
| 4,295,368 | 10/1981 | Jannone | 374/42 X |

FOREIGN PATENT DOCUMENTS 2727106 12/1978 Fed. Rep. of Germany ........ 374/42

*Primary Examiner*—Daniel M. Yasich
*Attorney, Agent, or Firm*—Robert A. Kulason; Henry C. Dearborn

[57] ABSTRACT

A method for determining the quality of steam flowing in a line used for steam injection, e.g. in an oil well. It has a vertical loop in the line, with an orifice in the up-flow side. The pressure, temperature and pressure drop at the orifice are measured before and after injecting a stream of water upstream from the orifice. The water stream is injected at a constant flow rate, and its temperature and pressure are measured. Using the measurements before and after the introduction of the water stream, simultaneous equations are developed related to the mass flow rate and to the heat flow rate, so that the steam quality may be determined.

7 Claims, 1 Drawing Figure

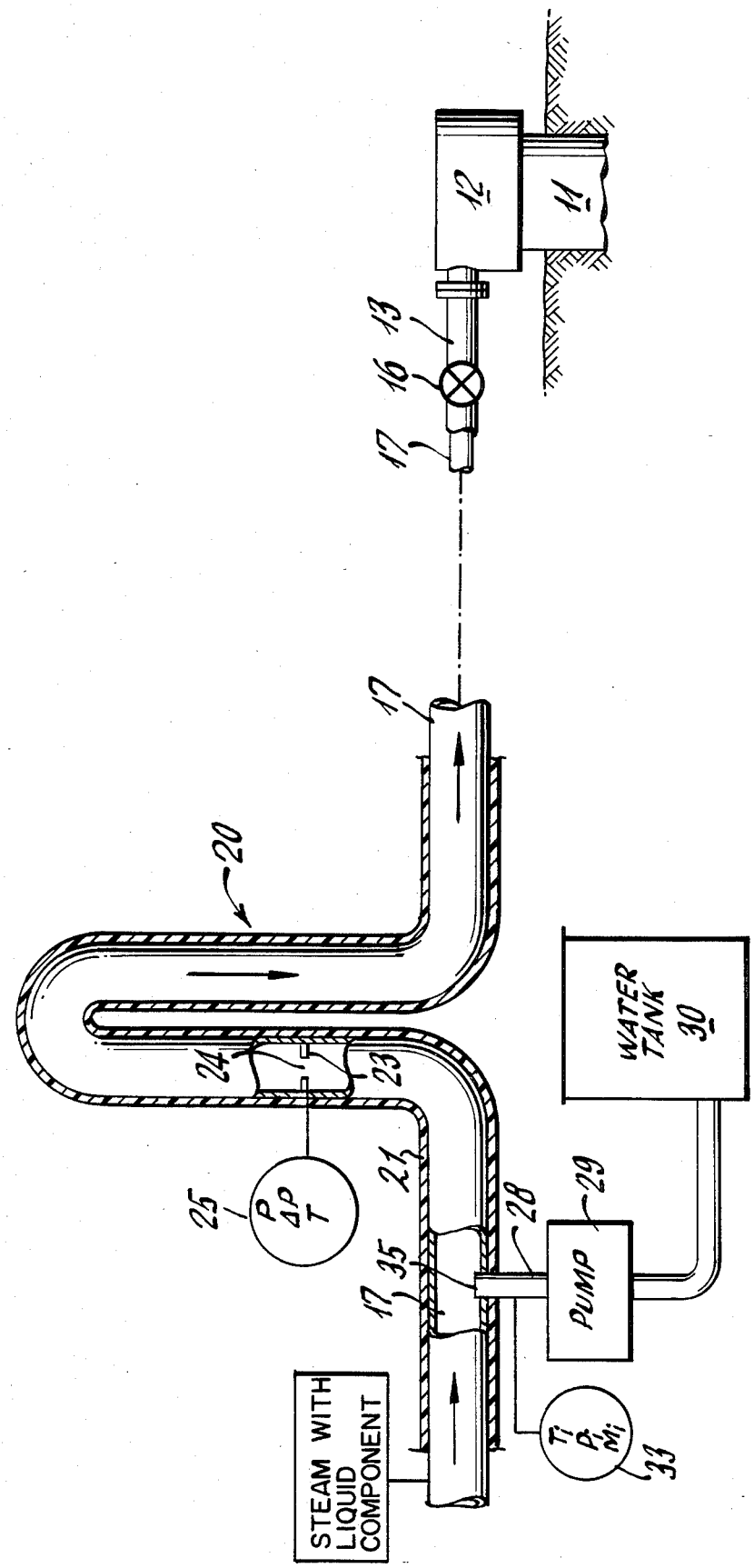

METHOD OF MEASURING QUALITY OF STEAM IN A FLOW FINE

FIELD OF THE INVENTION

This invention concerns a method for measuring quality of a gaseous fluid mixture that includes an unknown quantity of a liquid component. More specifically, it is concerned with a method for measuring the quality of steam in a flow line to an injection well in a steam flooding project for oil recovery.

BACKGROUND OF THE INVENTION

With the advent of steam flooding projects, i.e. in oil recovery from oil fields that need stimulation to produce the oil, there is a need for a simple method to determine the quality of steam at the well head of an injection well. Such a measurement would be particularly useful to determine the heat input to the underground reservoir. The measurement is important because steam quality directly affects production operations, earnings and future investment requirements. In the past, the desired information was not obtainable after a steam supply had been split by use of a manifold which separated the liquid and vapor components of the steam. However, by use of a method according to this invention, the quality measurements may be directly made individually for steam lines supplying each injection well.

BRIEF SUMMARY OF THE INVENTION

Briefly, the invention concerns a method of measuring the quality of a gaseous fluid mixture having an unknown quantity of a liquid component. It comprises the steps of passing said fluid mixture through an orifice, and measuring the pressure, the differential pressure and the temperature at said orifice of said fluid mixture. It also comprises the step of injecting a known quantity of said liquid component at a known temperature and pressure into said fluid mixture upstream of said orifice. And it comprises the steps of measuring the pressure, the differential pressure and the temperature at said orifice again, after said step of injecting, whereby said quality may be calculated.

Again briefly, the invention is in a steam injection procedure for recovering oil by introducing steam into one or more injection wells. It concerns a method of accurately determining the quality of steam being injected through a flow line, and it comprises the steps of introducing an orifice into said flow line, and measuring the static pressure the temperature and the pressure drop across said orifice. It also comprises the steps of injecting a quantity of water upstream from said orifice, and measuring the temperature the pressure and the mass flow of said quantity of water. It also comprises the steps of measuring the static pressure, the temperature, and the pressure drop across said orifice after said injecting of water upstream from said orifice, and determining the quality of steam being injected by solving simultaneous equations derived from said measurements before and after said water injection.

Once more briefly, the invention is in a steam injection procedure for recovering oil by introducing steam into one or more injection wells. It comprises a method of accurately determining the quality of steam being injected through a flow line to one of said injection wells, which comprises the steps of providing a vertical loop in said flow line for creating uniformity in cross section flow. It also comprises the steps of introducing an orifice into said flow line in the up-flow side of said loop at a point of uniform cross section flow, and measuring the static pressure the temperature and the temperature drop across said orifice. It also comprises the steps of injecting a stream of water at a constant rate upstream from said orifice and measuring the temperature the pressure and the liquid mass flow of said injected stream of water. It also comprises the steps of measuring the static pressure the temperature and the pressure drop across said orifice after steady state conditions following said injecting a stream of water at a constant rate, and determining the quality of steam being injected by solving simultaneous equations derived from mass flow rates and heat flow rates using Newton's Method.

BRIEF DESCRIPTION OF THE DRAWING

The foregoing and other objects and benefits of the invention will be more fully set forth below in connection with the best mode contemplated by the inventors of carrying out the invention, and in connection with which there are illustrations provided in the drawings, wherein;

The FIGURE of drawings illustrates a schematic indication of a steam flow line with elements that are employed therewith in order to carry out a method according to the invention. The schematic also shows an oil well-head with a steam injection pipe or line connected thereto.

DESCRIPTION OF THE PREFERRED EMBODIMENT

As indicated above, there has been a problem in steam flooding projects where steam is injected into oil wells, in order to stimulate the recovery of additional oil by the heating effects of the steam. It has not been feasible to determine steam quality at each individual injection well head. However, such knowledge is important because the steam quality directly effects the production operations and consequently the earnings and future investment requirements for steam flooding projects.

A method according to this invention provides for a simple and effective procedure that permits measurement of the steam quality in a flow line just prior to the introduction into a given injection well. An illustration of typical apparatus that may be employed to carry out the method is illustrated in the FIGURE of Drawings. As there illustrated, the steam injection procedure is used for recovering oil by introducing steam into an injection well 11. The well 11 has a well head 12 into which there is a pipe 13 connected. Also, there will be a valve 16 for controlling flow to or from the well 11.

In connection with a method according to this invention the pipe 13 has heat insulation which covers a steam flow line 17 through which the steam that is to be injected for the well stimulation procedure passes. The steam flow line 17 is illustrated somewhat enlarged and is schematically shown partially in longitudinal cross section on the left hand side of the drawing. This is in order to illustrate the fact that there is a vertical loop 20 in the flow line 17. Loop 20 provides a means for having the steam flow (particularly on the upflow side of the loop) develop a uniform flow pattern in cross section.

As indicated above, the pipe 13 that includes the steam flow line 17 is heat insulated. Thus, the steam flow line 17 is covered with a heat insulating layer 21 in order to minimize heat loss as the steam flows through the line. On the upflow side of the loop 20 there is a orifice 24 which is used in connection with making measurements that are used as the method is carried out. It will be understood that the orifice 24 may be formed by inserting a plate 23 or similar barrier, diametrically across the flow line 17. The plate 23 has a central opening or orifice 24 therein. It may be noted that there is a schematic indication of the measurements that are taken at the orfice 24. They are indicated in a circle 25 which has the letters P, ΔP and T inside. These indicate the measurements of static pressure, differential pressure and temperature, respectively.

Upstream from the orifice 24 there is a small pipe 28 that connects into the flow line 17. This is for introducing or injecting a stream of water during part of the procedure. In order for the injected flow of water to be at a constant rate, there is a pump 29 which draws its source of water from a water tank 30. When the water is being injected the measurements that are taken include the temperature, the pressure and the mass flow of the injected water. These measurements are schematically indicated by the symbols in a circuit 33 namely $T_i$, $P_i$ and $\dot{m}_i$.

It is known that by use of an orifice meter the quality of steam in a flow line can be determined if the mass flow rate is known. Also, if the quality is known the mass flow rate can likewise be determined. However, if both of the mass flow rate and the steam quality are unknown (which is frequently the case where a steam project has a steam supply provided through a manifold and then connected to various wells for injection), the orifice meter equation can not be solved. However, in accordance with our invention, a method involving use of an orifice in combination with injection of liquid makes it possible to determine both the quality and the mass flow rate of steam in a flow line. Such a method involves the following four steps.

1. Make a standard measurement of pressure, temperature and differential pressure across an orifice.

2. Upstream of the orifice, inject a liquid at known temperature, pressure and rate of flow.

3. Make measurements of pressure, temperature and differential pressure once steady state condition has been achieved after the liquid injection is underway.

4. Solve the orifice equation at two different conditions simulataneously for original quality and original mass flow rate.

A specific example of carrying out the method is described hereafter with reference to the schematic illustration of the drawing.

An insulated steam flow line 17 has an unknown quality steam flow proceeding therethrough in the direction of the arrows. It goes to the well 11 for injection in order to carryout a stimulation procedure. It will be noted that the illustration shows a layer of insulation 21 for providing heat insulation around the steam flow line 17.

At the orifice 24 the differential pressure (ΔP) and the pressure (P) as well as the temperature (T) of the flowing steam are measured. Upstream of the vertical pipe loop 20 there is an injection port 35 formed at the end of the pipe 28. At this point, water is injected into the flowing steam at a measured temperature $T_i$ and pressure $P_i$ as well as a mass flow rate $\dot{m}_i$ are measured. The pump 29 acts to inject the water from the storage tank 30 through the injection port 35 at the end of the pipe 28 into the flow line 17 at a constant rate.

The method may be explained in general mathematical form in accordance with the following. An orifice plate correlation may be written which expresses the relationship of steam quality to mass flow rate. However, such expression is only one equation and there are two unknowns:

$$X_1 = f_1(\dot{m}_1) \quad (1)$$

Where: $\dot{m}_1$ = mass flow rate of steam at initial conditions,
$X_1$ = steam quality at initial conditions and
$f_1$ = an empirical correlation function.

A second equation can be obtained by injecting liquid (water) into the two/phase gas-and-liquid (steam) to obtain a new equation as follows:

$$X_2 = f_2(\dot{m}_2) \quad (2)$$

Where: $m_2$ = mass flow rate of steam after injection of water started,
$X_2$ = steam quality after injection of water started, and
$f_2$ = a different or the same empirical correlation function.

In accordance with the foregoing it follows that the following equation expresses the mass flow rates involved:

$$\dot{m}_2 = \dot{m}_1 + \dot{m}_i \quad (3)$$

Where $\dot{m}_i$ = the measured injected mass flow rate of the liquid (water).

The heat flow rate at initial conditions may be expressed by the following equation:

$$q_1 = \dot{m}_1(h_{fg1}X_1 + h_{f1}) \quad (4)$$

Where $q_1$ = heat flow at initial conditions.
$h_{fg1}$ = latent heat of vaporization of water at initial conditions, and
$h_{f1}$ = sensible heat content of water at initial conditions.

The heat flow rate after constant water injection is started, may be expressed as:

$$q_2 = \dot{m}_2(h_{fg2}X_2 + h_{f2}) \quad (5)$$

Where $q_2$ = heat flow rate after constant water injection is started,
$h_{fg2}$ = latent heat of vaporization of water after constant water injection started, and
$h_{f2}$ = sensible heat content of water after constant water injection started.

Then, assuming negligible change in heat loss between the injection port (the water) and the orifice plate, the heat flow rate may be expressed as:

$$q_2 = \dot{m}_1(h_{fg1}X_1 + h_{f1}) + \dot{m}_1 h_{fi} \quad (6)$$

Where: $h_{fi}$ = sensible heat content of injected water. Then equations (3), (5) and (6) can be combined to express $X_2$ in terms of $X_1$ as follows:

$$\dot{m}_1(X_1 h_{fg1} + h_{f1}) + \dot{m}_i h_{fi} = (\dot{m}_1 + \dot{m}_i)(X_2 h_{fg2} + h_{f2}) \quad (7)$$

Since equations (3) and (7) express $m_2$ and $X_2$ in terms of $\dot{m}_1$ and $X_1$, there are two equations and two unknowns ($\dot{m}_1$ and $X_1$). However, these simultaneous equations may be solved using Newton's Method.

The method steps that are involved in the invention may be described in the following manner which is related to a steam injection procedure for recovering oil by introducing steam into one or more injection wells. The method is used for accurately determining the quality of steam that is being injected through a flow line to one of the injection wells, and it comprises the following steps.

(1) Providing a verticle loop in the flow line, e.g. the loop 20 illustrated in the drawing. This verticle loop is effective in creating uniformity of the cross section flow of the steam that is passing through the flow line.

(2) Introducing an orifice into the flow line in the up flow of the loop, at a point of uniform cross section flow. This is accomplished by the introduction of the plate 23 with orifice 24, that is spaced somewhat above the curve from the horizontal portion of flow line 17 to the up flow leg of the loop 20.

(3) Measuring the static pressure, the temperature and the pressure drop across the orifice. This step is carried out by conventional measuring instruments to determine the indicated static pressure and the pressure drop, as well as the temperature at the location of the orifice.

(4) A next step is that of injecting a stream of water at a constant rate upstream from the orifice. It will be understood that this injection of a water stream is carried out using the pump 29 to deliver a stream of water through the pipe 28 which is located in the stream flow line 17 on the up stream side of the loop 20. The flow of water will be regulated to have a constant rate.

(5) A next step is that of measuring the temperature, the pressure and the liquid mass flow of the injected stream of water. It will be understood that the temperature and the pressure measurements may be done with conventional instruments. Also, because the liquid mass flow of the water stream is directly related to the amount of water flowing (since it is an incompressible fluid) a conventional, rate of flow, meter will accomplish the necessary measurement.

(6) A next step is that of measuring the static pressure, the temperature and the pressure drop across the orifice after steady state conditions following the injection of the water stream at a constant rate. In this case, the same instruments will be employed to make the measurements under the changed conditions.

(7) A final step is that of determining the quality of steam being injected. The determination is accomplished by solving simultaneous equations that are derived from the mass flow rates and the heat flow rates involved in the two different flow conditions. Such simultaneous equations are solved using Newton's Method. It will be appreciated by any one skilled in the art that the step of solving simultaneous equations using Newton's Method will be greatly facilitated by making use of a computer type of calculator in order to carry out the iterative steps for arriving at a solution.

While a particular embodiment of the invention has been described above in considerable detail in accordance with the applicable statues, that is not to be taken as in any way limiting the invention but merely as being descriptive thereof.

We claim:

1. Method of measuring the quality of a gaseous fluid mixture flowing from a source thereof and having an unknown quantity of liquid component, comprising the steps of:

passing said fluid mixture through an orifice, measuring the pressure, the differential pressure across said orifice and the temperature at said orifice of said fluid mixture, injecting a known quantity of said liquid component, at a known temperature and pressure into said fluid mixture up stream of said orifice, and measuring the pressure, the differential pressure across said orifice and the temperature at said orifice again after said step of injecting, whereby said quality may be calculated by solving simultaneous equations derived from said measurements before and after said liquid component injection.

2. Method according to claim 1, wherein said step of injecting comprises pumping said liquid component at a constant flow rate while measuring the temperature and pressure thereof, and said step of measuring after injecting is carried out after conditions have stabilized.

3. In a steam injection procedure for recovering oil by introducing steam into one or more injection wells, a method of accurately determining the quality of steam being injected through a flow line to at least one of said injection wells, comprising:

introducing an orifice into said flow line, measuring the static pressure, the temperature and the pressure drop across said orifice, injecting a quantity of water upstream from said orifice, measuring the temperature the pressure and the mass flow of said quantity of water, measuring the static pressure, the temperature and the pressure drop across said orifice after said injecting of water upstream from said orifice, and determining the quality of steam being injected through said flow line by solving simultaneous equations derived from said measurements before and after said water injection.

4. In a steam injection procedure, a method according to claim 3, wherein said flow line has a vertical loop therein, and wherein said orifice is introduced into the up-flow leg of said loop.

5. In a steam injection procedure, a method according to claim 4, wherein said step of injecting water is at a constant rate, and said step of measuring after the injecting of water follows steady state conditions.

6. In a steam injection procedure, a method according to claim 5, wherein said step of injecting water is at substantially the same heat loss conditions as at said orifice.

7. In a steam injection procedure for recovering oil by introducing steam into one or more injection wells, a method of accurately determining the quality of steam being injected through a flow line to one of said injection wells, comprising the steps of providing a vertical loop in said flow line for creating uniformity in cross section flow, introducing an orifice into said flow line in the up-flow side of said loop at a point of uniform cross section flow, measuring the static pressure the temperature and the pressure drop across said orifice, injecting a stream of water at a constant rate upstream from said orifice, measuring the temperature the pressure and the liquid mass flow of said injected stream of water, measuring the static pressure the temperature and the pressure drop across said orifice after steady state conditions following said injecting a stream of water at a constant rate, and determining said quality of steam being injected by solving simultaneous equations derived from the measurements to obtain mass flow rates and heat flow rates before and after said water injection, using Newton's Method.

* * * * *